United States Patent

Doswald et al.

[11] Patent Number: 6,156,911
[45] Date of Patent: Dec. 5, 2000

[54] PURIFICATION OF LIPSTATIN

[75] Inventors: Stephan Doswald, Basel; Ernst Kupfer, Zürich, both of Switzerland; Gerhard Steinbauer, Enns; Erich Steinwender, Linz, both of Austria

[73] Assignee: Hoffmann-La Roche Inc., Nutley, N.J.

[21] Appl. No.: 09/491,557

[22] Filed: Jan. 26, 2000

[30] Foreign Application Priority Data

Jan. 29, 1999 [EP] European Pat. Off. .............. 99101893

[51] Int. Cl.$^7$ .................................................. C07D 305/12

[52] U.S. Cl. ........................................... 549/328; 549/263

[58] Field of Search ...................................... 549/328, 263

[56] References Cited

U.S. PATENT DOCUMENTS 4,598,089 7/1986 Hadvary et al. ........................ 514/449

FOREIGN PATENT DOCUMENTS 803 576 10/1997 European Pat. Off. .

Primary Examiner—Ba K. Trinh
Attorney, Agent, or Firm—George W. Johnston; William H. Epstein; John P. Parise

[57] ABSTRACT

The present invention relates to a method for the purification of the lipstatin. Impurities are removed from a lipstatin preparation by: a) mixing the preparation with a polar phase and to form a first two phase system in which the ratio of the lipstatin to the non-polar impurities in the polar phase is greater than in the preparation, and separating the phases from the first two phase system and collecting the lipstatin-enriched polar phase, and b) i) diluting the lipstatin-enriched polar phase from step a) with water to form a diluted lipstatin-enriched polar phase containing the polar solvent in a percentage of at least seventy percent of the polar phase and lower than in the lipstatin-enriched polar phase from step a), and mixing the diluted lipstatin-enriched polar phase with a second non-polar phase, the second non-polar phase being the same non-polar solvent as the first non-polar phase in the same or greater relative amount to the polar phase as in the first two phase system; or ii) mixing the lipstatin-enriched polar phase from step a) with a second non-polar phase, the second non-polar phase being the same non-polar solvent as the first non-polar phase in a greater relative amount to the polar phase as in the first two phase system; to form a second two phase system in which the ratio of the lipstatin to the polar impurities in the second non-polar phase is greater than in the lipid-enriched polar phase from step a), and separating the phases from the second two phase system and collecting the lipstatin-enriched second non-polar phase.

44 Claims, No Drawings

PURIFICATION OF LIPSTATIN

BACKGROUND OF THE INVENTION

Lipstatin is of considerable importance as key intermediate for the preparation of tetrahydrolipstatin (THL, Orlistat), which is useful in the prophylaxis and treatment of diseases associated with obesity.

Lipstatin, a fermentative process for its production, a process for its isolation from microorganisms and a process for its hydrogenation to tetrahydrolipstatin are known and described for example in U.S. Pat. No. 4,598,089.

Lipstatin is depicted as follows:

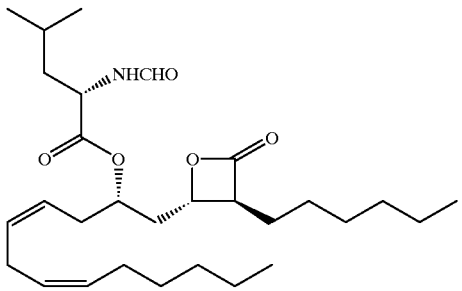

(I)

A process for the preparation of crude lipstatin has also been described in European Patent Application No. 96106598. This process comprises aerobically cultivating a microorganism of the order of actinomycetes, e.g. *Streptomyces toxytricini*, which produces lipstatin, in an aqueous medium which is substantially free of fats and oils, and which contains suitable carbon and nitrogen sources and inorganic salts, until the initial growth phase is substantially finished and sufficient cell mass has been produced. Then, linoleic acid together with an antioxidant, and optionally together with caprylic acid, and N-formyl-L-leucine or preferably L-leucine is added to the broth. After completion of the fermentation, the fermentation broth is extracted. The produced crude lipstatin can be further enriched and purified, e.g. by chromatographic methods, described in U.S. Pat. No. 4,598,089.

Multiple step chromatographic protocols or liquid-liquid extractions to enrich lipstatin in combination with multiple step chromatography to obtain pure lipstatin characterizes prior-art methods for the purification of crude lipstatin. These methods are typically used for the isolation of fermentation metabolites on a laboratory scale. However, these methods are generally not suitable for an economic large-scale process.

Attempts to purify crude lipstatin by distillation failed. Lipstatin is stable for several hours at 60° C., but because of its low vapor pressure ($7 \times 10^{-7}$ mbar) vacuum distillation (<2 mbar) at this temperature is not feasible. At higher temperature lipstatin is degraded by elimination of carbon dioxide.

Crude lipstatin can also be purified by crystallization of lipstatin at temperatures below −20° C. However expensive technical equipment for low temperature crystallization is required and yield of this crystallization strongly depends on the quality of crude lipstatin. Especially with low quality of crude lipstatin, lipstatin is obtained in low yield via crystallization.

SUMMARY OF THE INVENTION

This invention provides a process for preparing a solution of purified lipstatin from a preparation containing lipstatin, one or more polar impurities and one or more non-polar impurities, comprising: a) mixing the preparation with a polar phase and a first non-polar phase (wherein the first non-polar phase is a non-polar solvent selected from aliphatic hydrocarbons and aromatic hydrocarbons; and the polar phase is a polar solvent selected from carboxylic acids, alcohols, O-substituted monoethylene glycols, O-substituted oligoethylene glycols, O-substituted polyethylene glycols, diols, and dipolar aprotic solvents, wherein the polar solvent is undiluted or diluted with up to about twenty percent water) to form a first two phase system in which the ratio of the lipstatin to the non-polar impurities in the polar phase is greater than in the preparation, and separating the phases from the first two phase system and collecting the lipstatin-enriched polar phase; and b) either i) diluting the lipstatin-enriched polar phase from step a) with water to form a diluted lipstatin-enriched polar phase containing the polar solvent in a percentage of at least seventy percent of the polar phase and lower than in the lipstatin-enriched polar phase from step a), and mixing the diluted lipstatin-enriched polar phase with a second non-polar phase, the second non-polar phase being the same non-polar solvent as the first non-polar phase in the same or greater relative amount to the polar phase as in the first two phase system; or ii) mixing the lipstatin-enriched polar phase from step a) with a second non-polar phase, the second non-polar phase being the same non-polar solvent as the first non-polar phase in a greater relative amount to the polar phase as in the first two phase system; to form a second two phase system in which the ratio of the lipstatin to the polar impurities in the second non-polar phase is greater than in the lipid-enriched polar phase from step a), and separating the phases from the second two phase system and collecting the lipstatin-enriched second non-polar phase, thereby obtaining a lipstatin solution purified from the impurities present in the preparation.

The present invention provides a novel, simple, and inexpensive process for the purification of lipstatin from crude lipstatin in high yield and purity, even with low quality of the crude material.

DETAILED DESCRIPTION OF THE INVENTION

The following definitions are set forth to illustrate and define the meaning and scope of the various terms used to describe the invention herein.

The term 'double-current extraction' means a two-solvent counter-current extraction. The extraction is performed as shown in the following figure:

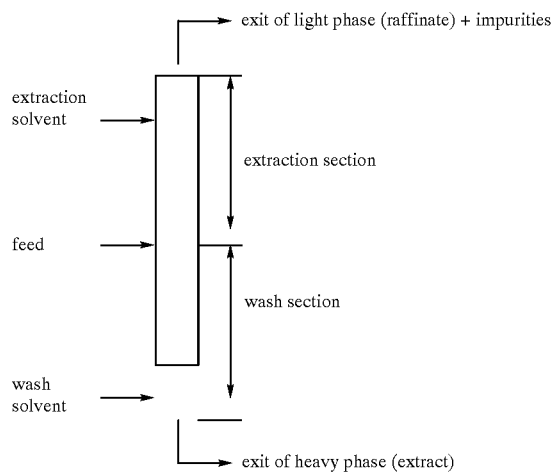

Two solvents whose mutual solubility is low are introduced at the top and bottom of the extraction unit. The mixture to be separated (feed) can be introduced anywhere, except in combination with the wash solvent, preferably in the middle of the extraction unit. In the above figure the extraction is performed in that form that the extraction solvent and the extract, respectively, contain the solvent with higher density (heavy phase) and the wash solvent and the raffinate, respectively, contain the solvent with lower density (light phase).

The term 'counter-current extraction' means that the substance to be extracted (feed) is added together with one of the solvents used. In that case separation of impurities from the compound to be purified is not as high as in the case of a double current extraction, as the wash section is omitted.

The counter current extraction is performed as shown in the following figure:

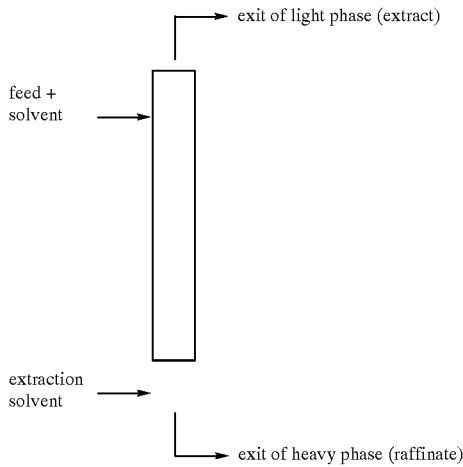

One solvent together with the feed and another solvent with low mutual solubility are introduced at the top and bottom of the extraction unit. At one exit the extraction solvent enriched with the target substance leaves the column (extract). At the other exit the solvent, which was used to introduce the feed, depleted in the target substance (raffinmte) leaves the column. In the above figure the extraction is demonstrated in that form that the feed and the raffinate, respectively, contain the solvent with higher density (heavy phase) and the solvent used for extraction and the extract, respectively, contain the solvent with lower density (light phase).

The purification process of this invention can use as its starting material any preparation, composition or mixture that contains lipstatin, one or more polar impurities and one or more non-polar impurities. Preferably the starting material is crude lipstatin. The term 'crude lipstatin' means the crude product containing lipstatin and impurities, resulting from the fermentation process after separation of the cell mass, extraction and concentration. The crude lipstatin can be crude lipstatin produced by any conventional fermentation process, for example the fermentation process described in U.S. Pat. No. 4,598,089.

The present invention relates to a method combining two liquid-liquid extractions, as means for isolating lipstatin from crude lipstatin in high purity and practically quantitative yield.

In general, the process for the purification of lipstatin from crude lipstatin comprises a liquid-liquid extraction of lipstatin from a non-polar solvent selected from an aliphatic or aromatic hydrocarbon into a polar solvent selected from a carboxylic acid, an alcohol, an O-monosubstituted mono- or oligo- or polyethyleneglycol, a diol or a dipolar aprotic solvent followed by diluting the polar solvent phase with water or changing the phase ratio and re-extraction of lipstatin into a fresh non polar solvent.

The liquid-liquid extractions are performed in the following solvent systems: The non-polar solvent is selected from an aliphatic or aromatic hydrocarbon. Preferred aliphatic hydrocarbons are $C_5$–$C_8$ aliphatic hydrocarbons, more preferably $C_6$–$C_7$ aliphatic hydrocarbons like hexane or heptane. Aromatic hydrocarbons may be selected from benzene, optionally substituted by 1 to 3 methyl-groups. Preferred aromatic hydrocarbons are benzene and toluene.

The polar solvent may be selected from carboxylic acids, e.g. formic acid or $C_1$–$C_3$ alkylcarboxylic acids, like acetic acid or propionic acid, or $C_1$–$C_3$ alcohols, like methanol, ethanol, propanol, or O-monosubstituted mono- or oligo- or polyethyleneglycols, like ethyleneglycol monomethylether or $C_2$–$C_3$ diols, like ethanediol or 1,3-propanediol, or furfuryl- or tetrahydrofurfurylalcohol. A dipolar aprotic solvent comprises solvents like dimethylformamide, N-methylpyrrolidone, dimethylsulfoxide, acetonitril, sulfolane, nitromethane etc. The preferred polar solvents are water soluble organic carboxylic acids, alcohols or O-monosubstituted mono- or polyethyleneglycols, for example acetic acid, methanol or ethylenegylcol monomethylether, especially preferred is acetic acid.

The polar solvent can be either used directly or as a mixture with water.

In the first extraction step non-polar and in the second extraction step polar impurities of crude lipstatin are removed. Extraction of lipstatin into a polar solvent results in removal of non-polar impurities and extraction of lipstatin into a non-polar solvent results in removal of polar impurities. The terms "polar" and "non-polar", for example in the expressions polar impurities and non-polar impurities, are used herein in accordance with the conventional meaning of these terms. Operationally, polar impurities are impurities present in the starting material that are more soluble in the polar solvent selected than in the non-polar solvent selected in accordance with the process of this invention. Non-polar impurities are impurities present in the starting material that are more soluble in the non-polar solvent selected than in the polar solvent selected in accordance with the process of this invention.

In a preferred embodiment the same solvents are used in both extractions. The first extraction is followed by a second step comprising diluting the polar solvent with water or changing the phase ratio, in order to change the distribution of lipstatin.

In a further preferred embodiment the first extraction is performed in such a way that lipstatin is extracted into the polar solvent followed by re-extraction of lipstatin from the polar solvent with a non-polar solvent, preferably the same non-polar solvent as used in the first extraction step.

In a preferred embodiment the liquid-liquid extraction of the first step is characterized in that the polar solvent contains about 1 to about 20% of water, more preferably about 5% of water.

In a further preferred embodiment, the non-polar solvent is an aliphatic hydrocarbon. Especially preferred is heptane.

In the most preferred embodiment of the present invention, the liquid-liquid extraction of the first step is performed as double-current extraction and lipstatin is extracted into the polar solvent. The feed is crude lipstatin, which may be diluted by one of the used solvents. Lipstatin is extracted into the polar (heavy) phase; non polar impurities like fatty acids or glycerides remain in the non-polar (light) phase.

The selection of non-polar solvent, polar solvent, degree of dilution of polar solvent in the first separation step, ratio of polar to non-polar phase and the like are not crucial to the successful operation of the process of this invention. However, as partition coefficients of lipstatin and impurities depend on concentration, phase ratio of the two solvents, number of theoretical stages of the extraction system and the ratio of feed to solvents have to be adjusted in an appropriate manner to optimize the process for yield and extent of purification. Dependence of the partition coefficient on concentration varies strongly with the kind of polar solvent used in the extraction system. Aqueous acetic acid gives very good results in order to achieve high concentration and therefore high throughput and a minimum of solvent used. Information useful in optimizing the process of this invention may be found in Lo, et al. (1983) Handbook of Solvent Extraction (Wiley, New York).

In accordance with this invention, the apparatus used is not crucial and any conventional apparatus for separating phases in liquid-liquid extractions can be used in each of the separation steps of this invention. Preferably the extraction can be carried out either by using a continuous extraction apparatus like a mixer settler system or an extraction column like a pulsed sieve plate extractor or a stirred column.

In the preferred embodiment prior to re-extraction (the second step of the purification) the polar solvent is diluted to approximately 70% to 90%, preferably to about 80% by addition of water.

In the most preferred embodiment of the present invention, the re-extraction of the second purification step is performed as counter-current extraction and lipstatin is extracted in the non-polar solvent. In that case the extract of the first extraction can be used directly. In contrast to a double current extraction, where a concentrated lipstatin feed is required, in the case of performing the second extraction as a counter current extraction in a continuous process, no concentration of lipstatin after the first extraction is necessary. Lipstatin is extracted into the non-polar (light) phase and polar impurities remain in the polar (heavy) phase.

During fermentation several amino acid analogues of lipstatin are formed. Lipstaitin itself contains N-formyl (S) leucine as a side chain, whereas the by-products contain other N-formyl amino acids. One of these by-products is the methionine-analogous lipstalin. Crude lipstatin contains up to 3% of this by-product relative to lipstatin. For purification of lipstatin it is of great importance to remove this impurity. Otherwise subsequent hydrogenation would be inhibited by this sulfur-containing compound. According to the present invention the purification of crude lipstatin is further improved, if the methionine-analogous lipstatin in crude lipstatin is oxidized prior to extraction. It is not possible to remove the methionine-analogous lipstatin directly by crystallization or extractive purification of lipstatin, except after oxidation to the corresponding sulfoxide or sulfone. This oxidation is done by a conventional method, for example by using peracetic acid in acetic acid. The methionine-analogous lipstatin can be either oxidized to the sulfoxide or to the sulfone:

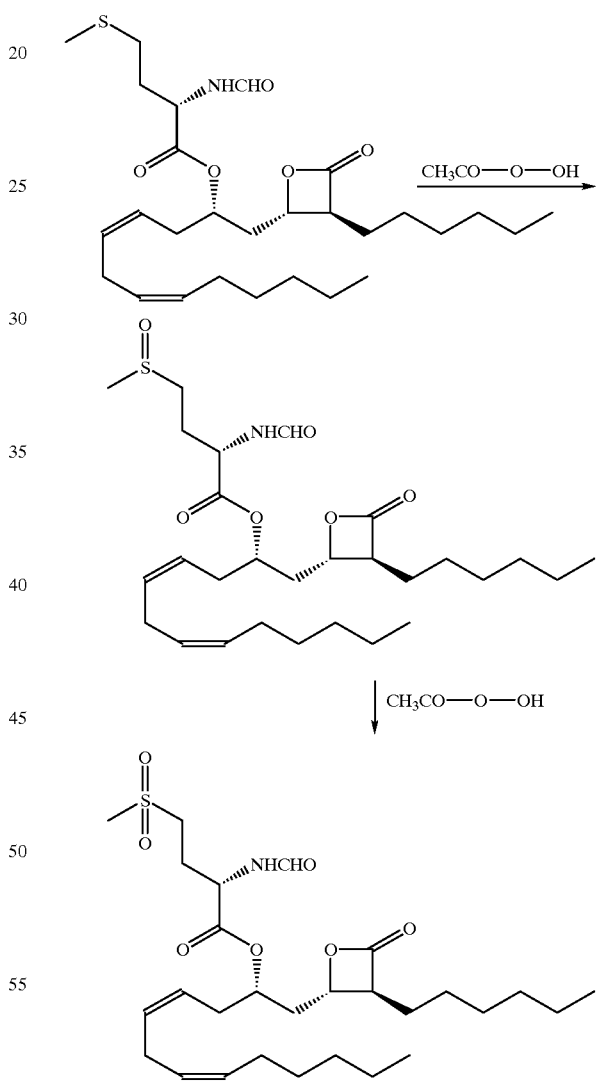

The oxidizing agent is used in an equimolar amount or up to 1.5 equivalents to the amount of methionine-analogous lipstatin, if the sulfoxide is required or the double amounts if the sulfone is required. Larger excess should be avoided to prevent oxidative degradation of lipstatin. The oxidation is performed at 0° to 50° C., preferably at room temperature; the reaction is completed in a few minutes. The solvent used for oxidation is not critical, preferably one of the solvents which are used during the extractive purification process is also used for oxidation. The methionine-analogous lipstatin may be oxidized either in the step of crude lipstatin or after the first extractive purification step. Preferably the oxidation is performed with crude lipstatin in heptane solution of high concentration and the resulting mixture is used as feed for the first extractive purification step. The oxidized methionine-analogous lipstatin is a polar impurity and is removed during the second extraction, where it remains in the polar phase.

It is sufficient that the second extraction step is performed as a counter current extraction using the extract from the first extraction step directly after addition of water, if the system aqueous acetic acid/heptane is used for extractive purification, due to the difference between the partition coefficients of lipstatin and the oxidized methionine-analogous lipstatin. Therefore in the most preferred embodiment, purification of lipstatin from crude lipstatin is achieved by double-current extraction of crude lipstatin in about 95% acetic acid/heptane, followed by dilution of the lipstatin solution with water to about 80% acetic acid and counter-current extraction of the solution with heptane. Purified lipstatin may then be isolated from heptane by concentration or crystallization. This preferred process is illustrated in the following scheme:

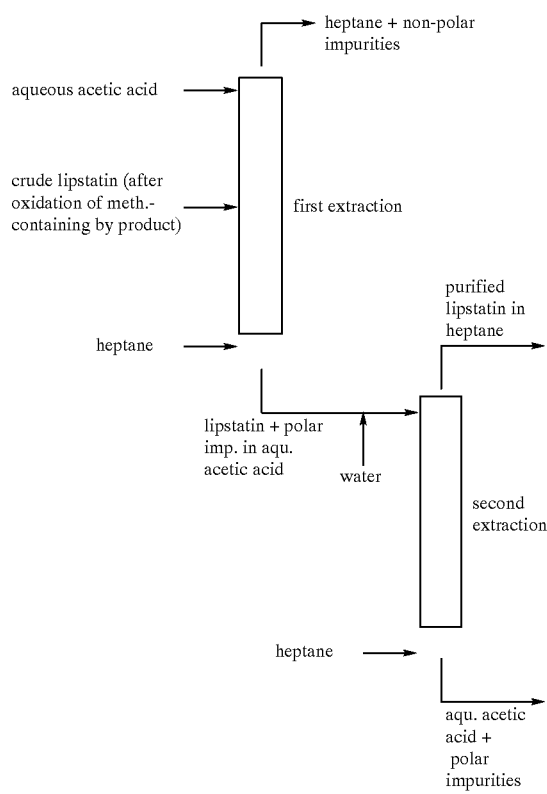

As pointed out above, lipstatin prepared by any of the processes as described above, may be converted to tetrahydrolipstatin (orlistat) by hydrogenation. The hydrogenation of lipstatin can be carried out according to methods which are known per se, e.g. as described in U.S. Pat. No. 4,598,089, in the presence of a suitable catalyst. Examples of catalysts which can be used are palladium/carbon, platinum oxide, palladium and the like. The solvent used for hydrogenation is not critical. The most preferred solvent is that used for the last extraction step. In that case the lipstatin containing extract is used directly or after concentration for hydrogenation. Other suitable solvents are, for example lower alcohols such as methanol and ethanol, ethers like tert.-butyl-methylether or tetrahydrofurane, acetic acid or halogenated solvents like dichloromethane. The hydrogenation is preferably carried out at low hydrogen pressures and at room temperature. Accordingly, the present invention also comprises the above extraction processes followed by hydrogenation of lipstatin to tetrahydrolipstatin. Preferably, the reaction is performed with a hydrogenation catalyst containing a precious metal at 25° C. at low hydrogen pressure. As used herein, "low hydrogen pressure" means from about 0.5 to about 5 bar (e.g. 5 bar).

Tetrahydrolipstatin may be purified and isolated by crystallization. Preferably a non-polar solvent like hexane or heptane is used for hydrogenation and crystallization.

In summary, the present invention relates to a process as defined above comprising
a) oxidation of methionine-analogous lipstatin
b) double-current extraction of crude lipstatin in about 95% acetic acid/heptane;
c) diluting the lipstatin solution with water to about 80% acetic acid; and
d) counter-current extraction of the solution with heptane.

This process may be followed by hydrogenation of lipstatin to tetrahydrolipstatin, optionally followed by crystallization of tetrahydrolipstatin.

The present invention also comprises a process for the preparation of tetrahydrolipstatin comprising
a) oxidation of methionine-analogous lipstatin
b) double-current extraction of crude lipstatin in about 95% acetic acid/heptane;
c) diluting the lipstatin solution with water to about 80% acetic acid; and
d) counter-current extraction of the solution with heptane, followed by
e) hydrogenation of lipstatin to tetrahydrolipstatin.

In addition, the invention relates to the use of the above methods for the preparation of lipstatin and tetrahydrolipstatin.

The contents of European Application No. 99101893.8, filed Jan. 29, 1999 are incorporated herein by reference.

The following examples shall illustrate preferred embodiments of the present invention but are not intended to limit the scope of the invention.

EXAMPLES

Example 1

Crude lipstatin from fermentation after separation of the biomass and extraction was concentrated. The material employed contained 58% (w/w) lipstatin (HPLC-analysis) and 0.9% (w/w) methionine-analogous lipstatin ($^1$H-NMR.-analysis).

a. Oxidation of methionine-analogous lipstatin: 55.7 g crude lipstatin were diluted with 77 ml heptane. 212 μl of a 37% solution of peracetic acid in acetic acid were added and the mixture stirred at room temperature for 30 minutes.

b. Double current extraction with heptane/95% aqueous acetic acid: for simulation of an extractor with 7 separation stages 7 separatory funnels were used.

The mixture resulting from the oxidation procedure described in a. was divided into 6 portions and each portion was fed into the 4$^{th}$ separatory funnel (sf-4). Starting with sf-4 feed, 50 ml heptane and 100 ml 95% aqueous acetic acid were added, which is equivalent to a phase ratio of heptane/aqueous acetic acid of 1/2. The mixture was shaken and the phases separated. The upper phase was transferred into the next and the lower phase into the previous separatory funnel. At the beginning fresh solvents were used, which were replaced step by step with phases from the previous and next separatory funnel. When all separatory funnels had been filled in this way, heptane was added in the 1$^{st}$ and aqueous acetic acid in the 7$^{th}$ separatory funnel only. Lipstatin containing extract was pooled. Lipstatin in the raffinate was monitored by thin layer chromatography to maintain its content below 1 g per liter and to control the precalculated phase ratio and concentration.

When all the crude lipstatin was fed, both unloaded solvents were added until all lipstatin was washed out of the system. The following scheme illustrates this extraction:

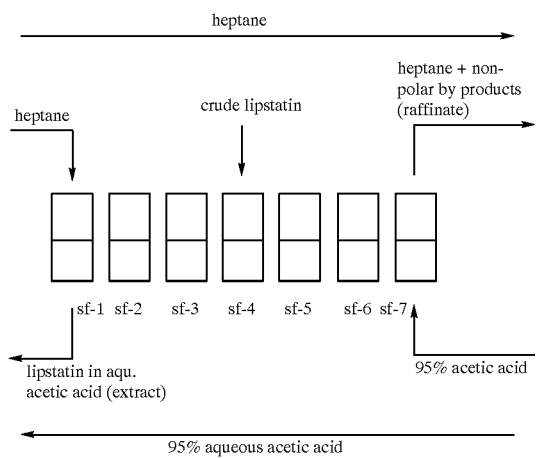

The extract was concentrated to a volume of about 600 ml by distilling off solvent under reduced pressure. Water content, determined by Karl Fischer method was 3.5%.

c. Counter current extraction: for simulation of an extractor with 7 separation stages again 7 separatory funnels were used.

The extract resulting from b. (600 ml) was divided into 6 portions (each 100 ml) and each portion together with 30 ml water added in the 7$^{th}$ separatory funnel. 130 ml heptane were added in the 1$^{st}$ separatory funnel. The extraction was performed as simulation of a continuous process similar to section b) by transfer of the upper phase to the following and the lower phase to the previous separatory funnel. Lipstatin in the raffinate was monitored by thin layer chromatography to maintain its content below 1 g per liter and to control the precalculated phase ratio and concentration. When all the extract solution from the first extraction step was fed, both solvents were added until all lipstatin was washed out. The following scheme illustrates this extraction:

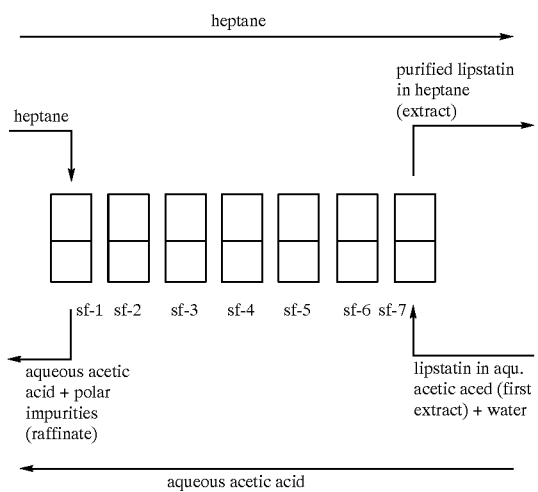

Purified lipstatin in heptane (extract) was pooled and concentrated under reduced pressure to a volume of 250 ml. This solution contained 35.3 g of purified lipstatin with a purity of 90% (w/w) (HPLC). This is equivalent to 98% yield calculated on the content of lipstatin in purified product, related to lipstatin in crude product.

d. Hydrogenation: The 250 ml solution of purified lipstatin was hydrogenated in a stainless steel autoclave at 25° C. at a pressure of 5 bar for totally 6 hours with 3.5 g 5% palladium on charcoal. The catalyst was filtered off and the filtrate evaporated. The residue was dissolved in 700 ml heptane and tetrahydrolipstatin crystallized at 0° C. The product was filtered, washed with cold heptane and dried in vacuo at 25° C. 28 g tetrahydrolipstatin of 96% (w/w) purity (HPLC) was obtained. This is equivalent to 85% yield, related to lipstatin in the purified product. The purity of tetrahydrolipstatin after recrystallization from hexane was 97% (w/w, by HPLC).

Example 2

A 7 stage mixer settler system was used for continuous extraction with the same solvents as used in example 1.

Concentrated crude lipstatin employed was of 65% (w/w) purity, containing 0.14% (w/w) of methionine-analogous lipstatin.

a. Double current extraction with heptane/95% aqueous acetic acid: 100 kg of crude lipstatin were diluted with 100 kg heptane and this solution used as feed. The mixer settler was filled with heptane and 95% aqueous acetic acid in a phase ratio of 1/2 (v/v). For extractive purification a feed of 37.5 liter per hour heptane, 75 liter per hour 95% aqueous acetic acid and 15 liter per hour solution of crude lipstatin were added. Heptane was introduced into the 1$^{st}$, lipstatin solution into the 4$^{th}$ and aqueous acetic acid into the 7$^{th}$ mixer. Lipstatin containing extract and non-polar impurities containing raffinate were collected. The content of lipstatin in the raffinate was monitored by thin layer chromatography to maintain the level below 1 g per liter. After feeding all the crude lipstatin, the feeding of both solvent was continued until all lipstatin was washed out. A sample of the extract (lower phase) was concentrated and gave lipstatin of 71% (w/w) purity. Totally, 1500 kg of extract was obtained, the water content was 4.6% (Karl Fischer method).

b. Oxidation of methionine-analogous lipstatin: To the extract solution from the previous extraction was added 60 ml of a solution of 37% peracetic acid in acetic acid and the mixture stirred for 30 minutes at room temperature.

c. Counter current extraction: 280 liter water were added to adjust a water content of 20%. Due to separation of an oily phase of lipstatin after adding water this solution was extracted with 600 liter of heptane. This extract was separated and later added to the heptane phase of the continuous extraction.

For the subsequent continuous extraction of the remaining solution of lipstatin in aqueous acetic acid the same mixer settler as at the first extraction was used. Continuous extraction was performed by feeding 50 liter per hour of heptane into the $1^{st}$ and 50 liter per hour of the solution of lipstatin in aqueous acetic acid into the $7^{th}$ mixer. The heptane extract was added to the extract obtained before and this solution concentrated to a volume of approx. 1000 liter by distilling off solvent under reduced pressure. A sample was concentrated to dryness affording lipstatin with 86% (w/w) purity.

d. Hydrogenation: The solution obtained was hydrogenated in 3 batches of the same size. Hydrogenation was performed in a glass lined stirred hydrogenation vessel. For one batch 2 kg of 5% palladium on charcoal was used. Hydrogenation was complete after 1 hour; hydrogen pressure reached 5 bar. The catalyst was filtered off and the filtrate concentrated by distilling off the solvent. A dried sample of the product contained 90% (w/w) tetrahydrolipstatin (the quality is higher than that of purified lipstatin, because lipstatin contains "convertible" by products, that are isomers with different position or only one C=C double bond, which are also transformed to tetrahydrolipstatin after hydrogenation). 600 kg of heptane were added and tetrahydrolipstatin crystallized at 0° C. The product was filtered off, washed with cold heptane and dried under reduced pressure.

One batch gave 17 kg of tetrahydrolipstatin of 97% (w/w) purity. This is equivalent to 76% yield of tetrahydrolipstatin, related to lipstatin in crude lipstatin.

Example 3

Crude lipstatin from fermentation after separation of the biomass and extraction was concentrated. The material contained 62% (w/w) lipstatin and 0.1% (w/w) methionine-analogous lipstatin.

a. Oxidation of methionine-analogous lipstatin: 53 g crude lipstatin was diluted with 75 ml heptane. 24 µl of a 37% solution of peracetic acid in acetic acid was added and the mixture stirred at room temperature for 30 minutes.

b. Double current extraction with heptane/10% aqueous methanol: The same system of 7 separatory funnels to simulate a continuous extraction was used as described in example 1. The mixture resulting from the oxidation procedure described in a) was divided into 6 portions and each portion was fed into the $4^{th}$ separatory funnel. 100 ml heptane was added into the $1^{st}$ and 10 ml of 10% aqueous methanol into the $7^{th}$ separatory funnel, which is equivalent to a phase ratio of heptane/aqueous methanol of 10/1. The extract (upper phase, lipstatin in heptane) was pooled. When all the crude lipstatin was led, both fresh solvents were further added until all lipstatin was washed out. The extract was concentrated to a volume of 110 ml by distilling off the solvent under reduced pressure.

c. Additional double current extraction with heptanel/10% aqueous methanol: The solution obtained from the above extraction was divided into 6 portions. With the same system of 7 separatory funnels as used before the same kind of extraction was performed, but with a different phase ratio. Each portion of feed was added into the $4^{th}$ separatory funnel. 100 ml heptane was added in the $1^{st}$ and 100 ml of 10% aqueous methanol into the $7^{th}$ separatory funnel, which is equivalent to a phase ratio of heptane/aqueous methanol of 1/1. The extract (lower phase, lipstatin in aqueous methanol) was pooled. When all the crude lipstatin was fed, both fresh solvents were further added until all lipstatin was washed out. The extract was concentrated to a volume of 250 ml by distilling off solvent under reduced pressure.

d. Batch extraction of lipstatin into heptane: Water was added to the extract solution obtained from c) to adjust a water content of 50%. This mixture was extracted twice with 600 ml heptane each. The extract was concentrated by distilling off solvent. 34 g lipstatin of 86% (w/w) purity was obtained. This is equivalent to 89% yield calculated on content of lipstatin in purified product, related to lipstatin in crude product.

e. Hydrogenation: Hydrogenation and crystallization were performed similar to example 1. Tetrahydrolipstatin was obtained with 97% (w/w) purity in 90% yield, related to lipstatin in the purified product.

Example 4

Using the same set up of a 7 stage extraction as described in example 3, crude lipstatin from the same batch as in example 3 was purified. Alternatively, 10% aqueous ethyleneglycolmonomethylether and heptane were used as solvents. Concentrations and phase ratios remained unchanged compared to example 3. A sample of lipstatin after purification had an assay of 80% (w/w). Hydrogenation and crystallization of tetrahydrolipstatin was performed as described in the previous examples. Tetrahydrolipstatin with a purity of 96% (w/w) was obtained.

Example 5

Crude lipstatin with an assay of 55% (w/w) lipstatin and 0.6% (w/w) methionine-analogous lipstatin was purified on a stirred Kuehni column.

a. Double current extraction with heptane/95% aqueous acetic acid: For the extraction a Kuehni column E60 with following dimensions was used: column I.D.: 6 cm, column height: 180 cm, number of practical stages: 50, stator plates free cross-section area: 10%. The column was stirred with 130 rpm. Fresh 95% aqueous acetic acid was fed as disperse phase with 1.75 l/h at the column top inlet. Fresh 95% aqueous acetic acid was fed as disperse phase with 4.0 l/h at the column top inlet. Fresh heptane was fed as continuous phase with 1.75 l/h at the column bottom inlet. A solution of 40% (w/w) crude lipstatin in heptane was fed with 0.775 kg/h at the $27^{th}$ practical stage (counted from the bottom) to the column. At equilibrium the yield of lipstatin in the extract phase at the column bottom outlet was >99% and the purity of lipstatin was 70% (w/w). The content of methionine-analogous lipstatin was 0.6% (w/w).

b. Oxidation with peracetic acid: The methionine-analogous lipstatin in the 95% aqueous acetic acid extract was oxidized by addition of an equimolar amount of 37% peracetic acid.

c. Counter current extraction with heptane/75% aqueous acetic acid: For the extraction a Kuehni column with the same dimensions as described under section a) was used. The column was stirred with 205 rpm. Lipstatin extract in 95% aqueous acetic acid (pool of several extraction batches, with a purity of 68% (w/w) lipstatin, prepared according section a)) was fed as disperse phase with 8.6 l/h at the column top inlet. Fresh deionized water was fed with 2.1 l/h at the 47th practical stage (counted from the bottom) of the column. Fresh heptane was fed as continuous phase with 6.0 l/h at the column bottom inlet. At equilibrium the yield of lipstatin in the extract phase at the column top outlet was 97% and the purity of lipstatin was 88% (w/w). This is equivalent to 96–97% yield calculated on content of lipstatin in purified product, related to lipstatin in crude product.

What is claimed is:

1. A process for preparing a solution of purified lipstatin from a preparation containing lipstatin, one or more polar impurities and one or more non-polar impurities, comprising:
   a) mixing the preparation with a polar phase and a first non-polar phase
      wherein the first non-polar phase is a non-polar solvent selected from aliphatic hydrocarbons and aromatic hydrocarbons; and the polar phase is a polar solvent selected from carboxylic acids, alcohols, O-substituted monoethylene glycols, O-substituted oligoethylene glycols, O-substituted polyethylene glycols, diols, and dipolar aprotic solvents, wherein the polar solvent is undiluted or diluted with up to about twenty percent water;
      to form a first two phase system in which the ratio of the lipstatin to the non-polar impurities in the polar phase is greater than in the preparation,
      and separating the phases from the first two phase system and collecting the lipstatin-enriched polar phase, and
   b) diluting the lipstatin-enriched polar phase from step a) with water to form a diluted lipstatin-enriched polar phase containing the polar solvent in a percentage of at least seventy percent of the polar phase and lower than in the lipstatin-enriched polar phase from step a), and mixing the diluted lipstatin-enriched polar phase with a second non-polar phase, the second non-polar phase being the same non-polar solvent as the first non-polar phase in the same or greater relative amount to the polar phase as in the first two phase system;
      to form a second two phase system in which the ratio of the lipstatin to the polar impurities in the second non-polar phase is greater than in the lipid-enriched polar phase from step a),
      and separating the phases from the second two phase system and collecting the lipstatin-enriched second non-polar phase,
      thereby obtaining a lipstatin solution purified from the impurities present in the preparation.

2. The process of claim 1, wherein the polar solvent in step a) is diluted with about 1 to about 20% water.

3. The process of claim 2, wherein the polar solvent in step a) is diluted with about 5% water.

4. The process according to claim 1, wherein the non-polar solvent is an aliphatic hydrocarbon.

5. The process according to claim 4, wherein the non-polar solvent is heptane.

6. The process according to claim 1, wherein the polar solvent is a carboxylic acid.

7. The process according to claim 6, wherein the polar solvent is acetic acid.

8. The process according to claim 1, wherein the polar solvent is an alcohol.

9. The process according to claim 8, wherein the polar solvent is methanol.

10. The process according to claim 1, wherein the polar solvent is an O-monosubstituted monoethyleneglycol or an O-monosubstituted oligoethyleneglycol.

11. The process according to claim 10, wherein the polar solvent is ethylenegylcol monomethylether.

12. The process according to claim 1, wherein the mixing and separation in step a) is performed by double-current extraction.

13. The process according to claim 1, wherein the polar solvent in step a) is undiluted or diluted with less than about 10% water and in step b) the diluted lipstatin-enriched polar phase contains the polar solvent in a percentage from about 90% to about 70% of the polar phase.

14. The process according to claim 9, where in step b) the diluted lipstatin-enriched polar phase contains the polar solvent in a percentage of about 80%.

15. The process according to claim 1, wherein the mixing and separation in step b) is performed by counter-current extraction.

16. The process of claim 1, wherein the preparation is crude lipstatin containing methionine analogous lipstatin.

17. The process according to claim 16, further comprising oxidizing the methidnine analogous lipstatin to the corresponding sulfoxide or sulfone prior to step a).

18. The process according to claim 17, further comprising treating the lipstatin-enriched second non-polar phase collected in step b) to hydrogenate the lipstatin to tetrahydrolipstatin.

19. The process of claim 18, wherein the hydrogenation reaction is performed with a hydrogenation catalyst containing a precious metal at 25° C. at low hydrogen pressure.

20. The process according to claim 17, wherein
   the mixing and separation in step a) is performed by double-current extraction;
   the polar solvent in step a) is about 95% acetic acid;
   the non-polar solvent is heptane;
   in step b) the lipstatin-enriched polar phase is diluted with water to about 80 % acetic acid; and
   the mixing and separation in step b) is performed by counter-current extraction.

21. The process according to claim 20, further comprising treating the lipstatin-enriched second non-polar phase collected in step b) to hydrogenate the lipstatin to tetrahydrolipstatin.

22. The process according to claim 21, further comprising treating the tetrahydrolipstatin-enriched second non-polar phase to crystallize the tetrahydrolipstatin, separating the crystalline tetrahydrolipstatin from the second non-polar phase, and collecting the crystalline tetrahydrolipstatin.

23. A process for preparing a solution of purified lipstatin from a crude lipstatin preparation containing lipstatin, one or more polar impurities including methionine analogous lipstatin, and one or more non-polar impurities, comprising:
   a) treating the preparation to oxidize any methionine analogous lipstatin present in the preparation to the corresponding sulfoxide or sulfone;
   b) mixing the crude lipstatin from step a) with a polar phase and a first non-polar phase to form a first two phase system in which the ratio of the lipstatin to the non-polar impurities in the polar phase is greater than in the preparation, and separating the phases from the first two phase system and collecting the lipstatin-enriched polar phase,
      wherein the first non-polar phase is heptane; the polar phase is 95%, acetic acid aqueous solution; and the mixing and separating in this step b) are performed by double-current extraction; and
   c) diluting the lipstatin-enriched polar phase from step b) with water to form a diluted lipstatin-enriched polar phase containing about 80% acetic acid, and mixing the diluted lipstatin-enriched polar phase with a second non-polar phase, the second non-polar phase being heptane in the same or greater relative amount to the polar phase as in the first two phase system;
to form a second two phase system in which the ratio of the lipstatin to the polar impurities in the second non-polar phase is greater than in the lipid-enriched polar phase from step b),
and separating the phases from the second two phase system and collecting the lipstatin-enriched second non-polar phase,
wherein the mixing and separating in this step c) are performed by counter-current extraction
thereby obtaining a lipstatin solution purified from the impurities present in the preparation.

24. A process for preparing tetrahydrolipstatin from a crude lipstatin preparation containing lipstatin, one or more polar impurities including methionine analogous lipstatin, and one or more non-polar impurities, comprising:

a) treating the preparation to oxidize any methionine analogous lipstatin present in the preparation to the corresponding sulfoxide or sulfone;

b) mixing the crude lipstatin from step a) with a polar phase and a first non-polar phase to form a first two phase system in which the ratio of the lipstatin to the non-polar impurities in the polar phase is greater than in the preparation, and separating the phases from the first two phase system and collecting the lipstatin-enriched polar phase,
wherein the first non-polar phase is heptane; the polar phase is 95% acetic acid aqueous solution; and the mixing and separating in step b) are performed by double-current extraction; and c) diluting the lipstatin-enriched polar phase from step a) with water to form a diluted lipstatin-enriched polar phase containing about 80% acetic acid, and mixing the diluted lipstatin-enriched polar phase with a second non-polar phase, the second non-polar phase being heptane in the same or greater relative amount to the polar phase as in the first two phase system;
to form a second two phase system in which the ratio of the lipstatin to the polar impurities in the second non-polar phase is greater than in the lipid-enriched polar phase from step b),
and separating the phases from the second two phase system and collecting the lipstatin-enriched second non-polar phase,
wherein the mixing and separating in step c) are performed by counter-current extraction, d) treating the lipstatin-enriched second non-polar phase from step c) to hydrogenate the lipstatin present therein to tetrahydrolipstatin; and e) treating the tetrahydrolipstatin-enriched second non-polar phase from step d) to crystallize the tetrahydrolipstatin, separating the crystalline tetrahydrolipstatin from the second non-polar phase, and collecting the crystalline tetrahydrolipstatin,
thereby preparing tetrahydrolipstatin from the crude lipstatin preparation.

25. A process for preparing a solution of purified lipstatin from a preparation containing lipstatin, one or more polar impurities and one or more non-polar impurities, comprising:

a) mixing the preparation with a polar phase and a first non-polar phase wherein the first non-polar phase is a non-polar solvent selected from aliphatic hydrocarbons and aromatic hydrocarbons; and the polar phase is a polar solvent selected from carboxylic acids, alcohols, O-substituted monoethylene glycols, O-substituted oligoethylene glycols, O-substituted polyethylene glycols, diols, and dipolar aprotic solvents, wherein the polar solvent is undiluted or diluted with up to 20% water;
to form a first two phase system in which the ratio of the lipstatin to the non-polar impurities in the polar phase is greater than in the preparation,
and separating the phases from the first two phase system and collecting the lipstatin-enriched polar phase, and b) mixing the lipstatin-enriched polar phase from step a) with a second non-polar phase, the second non-polar phase being the same non-polar solvent as the first non-polar phase in a greater relative amount to the polar phase as in the first two phase system,
to form a second two phase system in which the ratio of the lipstatin to the polar impurities in the second non-polar phase is greater than in the lipidi-enriched polar phase from step a),
and separating the phases from the second two phase system and collecting the lipstatin-enriched second non-polar phase,
thereby obtaining a lipstatin solution purified from the impurities present in the preparation.

26. The process of claim 25, wherein the polar solvent in step a) is diluted with about 1 to about 20% water.

27. The process of claim 26, wherein the polar solvent in step a) is diluted with about 5% water.

28. The process according to claim 25, wherein the non-polar solvent is an aliphatic hydrocarbon.

29. The process according to claim 28, wherein the non-polar solvent is heptane.

30. The process according to claim 25, wherein the polar solvent is a carboxylic acid.

31. The process according to claim 30, wherein the polar solvent is acetic acid.

32. The process according to claim 25, wherein the polar solvent is an alcohol.

33. The process according to claim 32, wherein the polar solvent is methanol.

34. The process according to claim 25, wherein the polar solvent is an O-monosubstituted monoethyleneglycol or an O-monosubstituted oligoethyleneglycol.

35. The process according to claim 34, wherein the polar solvent is ethylenegylcol monomethylether.

36. The process according to claim 25, wherein the mixing and separation in step a) is performed by double-current extraction.

37. The process according to claim 25, wherein the mixing and separation in step b) is performed by counter-current extraction.

38. The process of claim 25, wherein the preparation is crude lipstatin containing methionine analogous lipstatin.

39. The process according to claim 38, further comprising treating the crude lipstatin preparation to oxidize the methionine analogous lipstatin to the corresponding sulfoxide or sulfone prior to step a).

40. The process according to claim 39, further comprising treating the lipstatin-enriched second non-polar phase collected in step b) to hydrogenate the lipstatin to tetrahydrolipstatin.

41. The process of claim 40, wherein the hydrogenation reaction is performed with a hydrogenation catalyst containing a precious metal at 25° C. at low hydrogen pressure.

42. The process according to claim 39, wherein the mixing and separation in step a) is performed by double-current extraction;

the polar solvent in step a) is about 95% aqueous acetic acid;

the non-polar solvent is heptane;

in step b) the lipstatin-enriched polar phase is diluted with water to about 80% aqueous acetic acid; and the mixing and separation in step b) is performed by counter-current extraction.

43. The process according to claim 42, further comprising treating the lipstatin-enriched second non-polar phase collected in step b) to hydrogenate the lipstatin to tetrahydrolipstatin.

44. The process according to claim 43, further comprising treating the tetrahydrolipstatin-enriched second non-polar phase to crystallize the tetrahydrolipstatin, separating the crystalline tetrahydrolipstatin from the second non-polar phase, and collecting the crystalline tetrahydrolipstatin.

* * * * *